(12) United States Patent
Muscato et al.

(10) Patent No.: US 7,045,149 B2
(45) Date of Patent: May 16, 2006

(54) RUMINAL FLUID INOCULATION OF CALVES

(75) Inventors: Thomas V. Muscato, Candor, NY (US); James B. Russell, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 622 days.

(21) Appl. No.: 09/968,144

(22) Filed: Oct. 1, 2001

(65) Prior Publication Data

US 2002/0048607 A1    Apr. 25, 2002

Related U.S. Application Data

(63) Continuation-in-part of application No. 09/391,775, filed on Sep. 8, 1999, now Pat. No. 6,296,879.

(51) Int. Cl.
*A61K 35/38* (2006.01)

(52) U.S. Cl. .................. 424/551; 424/550; 424/535; 424/781

(58) Field of Classification Search ................ 424/551, 424/550, 535, 780
See application file for complete search history.

(56) References Cited

U.S. PATENT DOCUMENTS

| | | | |
|---|---|---|---|
| 2,700,611 A | | 1/1955 | Jeffreys |
| 4,172,127 A | * | 10/1979 | Huber |
| 4,644,056 A | | 2/1987 | Kothe et al. |
| 4,816,252 A | | 3/1989 | Scott et al. |
| 4,834,974 A | | 5/1989 | Scott et al. |
| 5,198,213 A | | 3/1993 | Scott et al. |
| 5,670,196 A | | 9/1997 | Gregory |
| 5,785,990 A | * | 7/1998 | Langrehr |

FOREIGN PATENT DOCUMENTS

| | | |
|---|---|---|
| DE | DT2621436 A1 | 12/1977 |
| WO | WO 93/11220 | 6/1993 |

OTHER PUBLICATIONS

Allison et al. Journal of Animal Science (1964), vol. 23, pp. 1164-1171.*

Ziolecka, A., Osinska, Z., and Ziolecka, A.: "The Effect of Stabilized Rumen Extract on Growth and Development of Caves. 1. Liveweight Gain and Efficiency of Feed Utilization." Zeitschrift Fuer Tierphysiologie Tierernaehrung Und Futtermittelkunde, vol. 51, No. 1-2, 1984, pp. 13-20, Berlin, DE.

Ikemori, Y et al.: "Passive Protection of Neonatal Calves Against Bovine Conronavirus-induced Diarrhea by Administration of Egg Yolk of Colostrum Antibody Powder." Veterinary Microbiology, vol. 58, 1997, pp. 105-111.

Ikemori, Y et al.: "Protection of Neonatal Calves Against Fatal Enteric Colibacillosis by Administration of Egg Yolk Powder from Hens immunized With K99-Piliated Enterotoxigenic *Escherichia Coli*" Am J Vet Res, vol. 53, No. 11, Nov. 1992, pp. 2005-2008.

Abe, F. : "Effect of Administration of Bifidobacteria and Lactic Acid Bacteria of Newborn Calves and Piglets." J Dairy Sci, vol. 78, No. 12, 1995, pp. 2838-2845.

Mee, J. et al.: "Effect of a Whey Protein Concentrate Used as a Colostrum Substitute in Calf Immunity, Weight Gain, and Health." Journal of Dairy Science, vol. 79, No. 5, 1996.

Selim, S.A. et al.: "Passive Immunotherapy in Neonatal Calves-1. Safety and Potency of a J5 *Escherichia Coli* Hyperimmune Plasma in Neonatal Calves." Vaccine, vol. 13, No. 15, 1995, pp. 1449-1453.

Vanbelle, M. et al.: "Probiotics in Animal Nutrition: a Review." Arch. Anim. Nutr., Berlin 40, 1990, pp. 543-567.

Roth, L.: "The Uses of Fastrack® Direct-Fed Microbial Products by the Dairy Industry" http://users.1st.net/AsOne/Dairydfm.htm. accessed Apr. 20, 1999.

Database WPI, Section ch, Week 2000380, Derwent Publications Ltd., London, GB; Class B04, AN 2000-440103, XP002181946 & RU 2 138 256 C (Lazarev A V), Sep. 27, 1999.

* cited by examiner

Primary Examiner—Susan D. Coe
(74) *Attorney, Agent, or Firm*—Wall Marjama & Bilinski LLP

(57) ABSTRACT

A method to improve the health and growth of suckling dairy calves on dairy farms includes supplementing calves' diets with a ruminal fluid preparation obtained from the rumen of a cow. This supplement provides the calves with the protection needed to develop faster and healthier. It also leads to a decreased incidence of scours in the treated calves.

20 Claims, 4 Drawing Sheets

Figure 1

|  | IBW (kg) | BWG (kg) | | | BWG Contrasts[1] | |
| --- | --- | --- | --- | --- | --- | --- |
|  | 0 wk | 0 to 2 wk | 2 to 4 wk | 4 to 6 wk | L | Q |
| Experiment 2 |  |  |  |  |  |  |
|   Control - C | 45.1 | 3.7 | 10.0 | 10.0 | *** | *** |
|   RFC (42 d) | 42.9 | 6.7 | 10.7 | 9.2 | *** | *** |
|   RFS (42 d) | 42.9 | 7.2 | 9.8 | 9.7 | *** | NS |
|   Contrasts: |  |  |  |  |  |  |
|     IBW  C x (RFC+RFS) | NS |  |  |  |  |  |
|     IBW  RFC x RFS | NS |  |  |  |  |  |
|     Gain  C x (RFC+RFS) |  | *** | NS | NS |  |  |
|     Gain  RFC x RFS |  | NS | NS | NS |  |  |
| Experiment 3 |  |  |  |  |  |  |
|   Control - C | 43.8 | 3.3 | 8.2 | 10.0 | *** | NS |
|   ARF (42 d) | 43.9 | 7.2 | 9.5 | 9.3 | NS | NS |
|   Contrasts: |  |  |  |  |  |  |
|     IBW  C x ARF | NS |  |  |  |  |  |
|     Gain  C x ARF |  | *** | NS | NS |  |  |
| Experiment 4 |  |  |  |  |  |  |
|   Control - C | 44.4 | 2.4 | 8.9 | 10.8 | *** | ** |
|   ARF (5 d) | 45.3 | 4.8 | 9.2 | 10.8 | *** | NS |
|   Contrasts: |  |  |  |  |  |  |
|     IBW C x ARF | NS |  |  |  |  |  |
|     Gain C x ARF |  | ** | NS | NS |  |  |

NS = non significant
** = $P < 0.01$
*** = $P < 0.001$
[1]Polynomial contrasts: L = linear and Q = quadratic effects.

Figure 2

|  | Growth Period (wks) | | | Scour |
| --- | --- | --- | --- | --- |
|  | 0 to 2 | 2 to 4 | 4 to 6 | Days[1] |
| Experiment 1 | | | | |
| Control | 10 | 3 | 5 | 2.67[a] |
| FRF (42 d) | 6 | 1 | 0 | 0.83[b] |
| Experiment 2 | | | | |
| Control | 12 | 5 | 2 | 2.75[a] |
| RFS (42 d) | 4 | 3 | 0 | 0.58[b] |
| RFC (42 d) | 5 | 1 | 0 | 0.50[b] |
| Experiment 3 | | | | |
| Control | 4 | 7 | 5 | 1.83[a] |
| ARF (42 d) | 3 | 1 | 0 | 0.33[b] |
| Experiment 4 | | | | |
| Control | 12 | 3 | 2 | 3.67[a] |
| ARF (5 d) | 3 | 1 | 0 | 0.42[b] |

[1]Means within a column for each experiment with different superscripts differ ($P < 0.05$, Kruskal-Wallis test).

Figure 3

|  | Weight gain (kg), wks | | | Contrasts[1] | |
| --- | --- | --- | --- | --- | --- |
|  | 0 to 2 | 2 to 4 | 4 to 6 | L | Q |
| Control - C | 3.6 | 9.5 | 10.7 | *** | *** |
| RF-Treated | 6.9 | 10.3 | 10.2 | *** | *** |
| Contrasts[1]: |  |  |  |  |  |
| C x Treated | *** | NS | NS |  |  |

NS = non significant
** = $P < 0.01$
*** = $P < 0.001$
[1]Polynomial contrasts: L = linear and Q = quadratic effects.

Figure 4

| Material | RFC | RFS |
|---|---|---|
| Volatile fatty acids | | |
| Acetate (mM) | < 2 | 48 ± 2 |
| Propionate (mM) | <1 | 13 ± 2 |
| Butyrate (mM) | <0.5 | 8 ± 1 |
| Cellular components | | |
| Protein (µg/ml) | 1490 ± 65 | 73 ± 25 |
| RNA (µg/ml) | 190 ± 27 | < 10 |
| DNA (µg/ml) | 16 ± 5 | < 10 |
| BPS (µg hexose equiv./ml) | 333 ± 10 | 260 ± 19 |

US 7,045,149 B2

RUMINAL FLUID INOCULATION OF CALVES

REFERENCE TO RELATED APPLICATIONS

This is a continuation-in-part patent application of copending application Ser. No. 09/391,775, filed Sept. 8, 1999 now U.S. Pat. No. 6,296,979, entitled "RUMINAL FLUID INOCULATION OF CALVES". The aforementioned application is hereby incorporated herein by reference.

ACKNOWLEDGMENT OF GOVERNMENT SUPPORT

This invention was made with Government support under Grant No. 1907-31000-002-00D, awarded by the USDA-ARS. The government has certain rights in the invention.

BACKGROUND OF THE INVENTION

1. Field of the Invention

The present invention pertains to the field of dairy farming. More particularly, the invention pertains to a method of treating neonate (new born) dairy calves with ruminal fluid preparations to improve their health and growth.

2. Description of Related Art

New-born, milk-fed calves on dairy farms are often severely affected by diarrhea commonly called "scours" (Davis and Drackley, 1998). Dairymen have implemented a variety of strategies to decrease the incidence of scours, including: 1) improvements in sanitation, 2) the use of individual hutches to decrease pathogen transmission, 3) oral antibiotics to combat bacterial infections, and 4) fortified colostrum supplements that may enhance passive immune defenses (Otterby and Linn, 1981). However, recent surveys indicate that calf mortality in the U.S. still ranges from 8 to 11% (National Animal Health Monitoring System, 1993, 1996).

Dairy calves are subjected to an environment rich in pathogenic bacteria and microbial agents soon after birth. The calves are inherently susceptible to these agents because they are essentially born without natural immunity. As a result, infectious diseases are the main cause of calf morbidity and mortality during their first few weeks of life. Calves are often given low levels of antibiotics as growth promotants, or larger doses as veterinary therapy, but widespread use of antibiotics in the animal industry has been criticized, and dairy calf mortality still is high (i.e., 8 to 11%).

The death rate of calves can be decreased by the passive transfer of immunoglobulin from the mother cow to the new calf. This passive transfer can be achieved naturally by colostrum. Colostrum is the milk secreted for the first few days after birth and is characterized by high protein and antibody content. However, calves can only absorb antibodies soon after birth, and efforts to transfer immunity through colostrum are often unsuccessful.

At times, more than 30% (Donovan et al., "Factors influencing passive transfer of dairy calves," *J Dairy Sci.* 69: 754–759, 1986; Norheim, et al., "An epidemiological studies of factors affecting serum IgG levels in dairy calves," *Nord. Vet.* 37: 121–135, 1985) of newborn calves do not develop immunity, or experience failure in passive transfer (McGuire et al., "Failure of colostral immunoglobulin transfer in calves dying from infectious disease," *J Am. Vet. Med. Assoc.* 169: 713–718, 1976; McEwan et al., "Observations on the immune globulin levels of neonatal calves and their relationship to disease," *J Comp. Pathol.* 80: 259–265, 1970; Gay et al., "Gamma globulin levels and neonatal mortality in market calves," *Vet. Rec.* 77: 148–149, 1965).

The passive immunity of new-born calves is boosted by colostrum, so the dairy industry has developed colostrum-based products that are purported to enhance the immune system. Because natural microflora protect calves from pathogens, lactic acid bacteria have been used as probiotics. Probiotics are bacteria which colonize the digestive tract and prevent colonization of pathogenic organisms.

When calves are exposed to pathogenic agents, diarrhea can cause severe dehydration, and in many cases, the calves die from dehydration rather than microbial infection per se (Tizard, 1996; Davis and Drackley, 1998). Newborns are very prone to diarrhea, and this condition is triggered by any agent that irritates the intestine (Guyton, 1971). Intestinal irritation increases secretion, motility, and stool volume. As the animal becomes older and the intestine is repeatedly exposed to irritants and antigens, the intestinal tissues become desensitized, and the frequency of diarrhea declines (Ernst et al., 1988).

Intestinal de-sensitization (sometimes called oral tolerance) is a localized phenomenon that is mediated by circulating immunoglobulins and macrophages (Fahmi and Chaby, 1993, 1994). When macrophages are presented with antigens bound to immunoglobulins, they secrete cytokines that can directly affect mammalian cells (Kaufman et al., 2000). Cytokines appear to accelerate intestinal maturation and desensitization, and this process is dose-dependent. Studies with food allergens have shown that low doses invoke limited suppression, but large doses can provoke clonal anergy and immunotolerance (Roitt, 1998; Tizard, 1996).

In nature, the calf is in constant contact with the mother cow. The mother frequently licks the muzzle of the calf, and this "grooming" is a source of ruminal microorganisms. When reared on dairy farms, the calves typically are removed from the mother so that grooming is no longer possible. Calves that are taken from the mother at birth and reared in isolation lack ruminal protozoa, but these animals eventually develop a ruminal flora that contains bacteria. Ruminal fluid has never been used as a milk additive for suckling dairy calves. Because ruminal fluid has a highly diverse population of bacteria and other microorganisms (Krause and Russell, 1996), it contains dozens, perhaps hundreds, of different bacterial polysaccharide molecules that can: 1) promote intestinal desensitization, 2) decrease diarrhea, 3) prevent dehydration and 4) enhance the health of calves.

Other methods of combating calf diarrheas have not been effective. Some workers have sought to enhance or fortify the mother cow's colostrum by immunizing the cow prior to calving. An alternative to colostrum is the immunization of very young calves with conventional vaccines. However, this often fails to offer the broad protection a newborn calf needs (Selim et al., "The effect of *Escherichia coli* J5 and modified live *Salmonella dublin* vaccines in artificially reared neonatal calves," *Vaccine* 13; 381–390, 1995; Husband and Lascelles, "Antibody responses to neonatal immunization in calves," *Res. Vet. Sci.* 18: 201–207, 1975).

The sanitation and air quality of calf facilities have improved and calves are frequently isolated in "hutches" to inhibit the transmission of pathogens. However, calf health and morbidity continues to be a serious problem for the dairy cattle industry. Calves can be given low levels of antibiotics as growth promotants or larger doses as veterinary therapy, but widespread use of antibiotics in the animal industry has been criticized by the human medical field.

U.S. Pat. No. 5,785,990 to Langrehr discloses a feed fortifier and enhancer for pre-ruminant calves and a method of using the same. The inventor claims a feed fortifier containing many components. This feed fortifier results in a reduced incidence and severity of scours, a condition also studied by the present inventors as a measure of health. Generally, the patent claims that the overall health of the calves improved. However, the patent does not disclose the specific use of ruminal fluid in the feed fortifier.

U.S. Pat. No. 5,670,196 to Gregory discloses a method for microfiltration of milk or colostral whey. The invention provides a method of microfiltering milk, milk serum, colostrum, or colostral serum which provides effective bioburden reduction without substantial loss of immunoglobulins, substantially reducing the bioburden in the product while providing high immunoglobulin yields. The method makes use of charged depth filters to provide consistent bioburden control, resulting in whey products fortified with immunoglobulins.

U.S. Pat. No. 5,198,213 to Stott et al. discloses a method of disease treatment utilizing an immunologically whey fraction. The whey is ultrafiltered through one or more different process steps to yield a filtered product having a concentration of immunologically active immunoglobulin of at least about seven percent of total solids. The filtered product is periodically tested to verify its activity to a specified microbe. The filtered product is orally administered in a therapeutically effective dose to an animal to treat a disease.

U.S. Pat. No. 4,834,974 to Stott et al. discloses an immunologically active whey fraction and recovery process. A dry, immunologically active filtered product is produced through the controlled one or two stage ultrafiltration of liquid whey containing immunologically active immunoglobulin (Ig). When fed to newborn calves, the product functions as a substitute for natural colostrum, providing both temporary passive immunity as well as initiation of the active immune system of the animal. Disease resistance and growth rate in animals, including humans, is enhanced by oral administration of the filtered product.

U.S. Pat. No. 4,816,252 to Stott et al. discloses a product and process for transferring passive immunity to newborn domestic animals using ultrafiltered whey containing immunoglobulins. Active immunoglobulins are extracted from the whey byproduct of dairy manufacturing, using ultrafiltration techniques to separate the large immunoglobulin molecules from the whey. The ultrafiltration retentate is dried to produce a filtered product having a high concentration of immunoglobulins. The dry filtered product is fed to newborn animals to transfer passive immunity. The whey-derived product is optionally used on a continuous basis as a food supplement for an animal to enable the immunologically active immunoglobulin molecules in the product to attack pathogens present in the digestive system of the animal.

U.S. Pat. No. 4,644,056 to Kothe et al. discloses a method of preparing a solution of lactic or colostric immunoglobulins or both, and use thereof, by processing milk or colostrum accompanied by precipitation of the caseins. The object of the invention is to provide a simple and economical method of preparing a solution of lactic or colostric immunoglobulins. A preferred starting material for the method in accordance with the invention is accordingly either colostrum from non-hyperimmunized mammals or human colostrum, with colostrum obtained from cows up to 30 hours after calving, with up to 5 hours after calving being particularly preferred.

Abe et al, *J Dairy Sci.* 78(12): 2838–46 (1995 Dec.) disclose that live preparations of bifidobacteria and lactic acid bacteria can be used as "probiotics." The bacteria are orally administered, resulting in an improvement in the general health of the calves receiving the bacteria. The article does not discuss or propose the use of a preparation of ruminal fluid in treatment of newborn calves.

Ruminal bacteria have a thick coating of bacterial polysaccharide (BPS) (Costerton et al., 1974), but the impact of this material on the ruminant immune system largely has been ignored. Work with various animals indicates that BPS is not only a trigger for antibody production, but in addition BPS can: 1) act as an adjuvant to enhance the potency other antigens, 2) induce macrophages to release cytokines that affect the differentiation of mammalian cells, and 3) circumvent the normal cascade of immunostimulation to cause an anergy commonly called oral tolerance (Tizard, 1996; Roitt et al., 1998).

SUMMARY OF THE INVENTION

Briefly stated, the present invention provides a method to improve the health and growth of suckling dairy calves that includes supplementing the calves' diets with a ruminal fluid preparation obtained from the rumen of a mature cow. This supplement provides the calves with the protection needed to grow faster and healthier. It also leads to a decreased incidence of scours (diarrhea) in the treated calves.

According to one embodiment, the present invention provides a method of improving the health of dairy calves, including the steps of withdrawing ruminal fluid from the rumen of a mature cow, sterilizing the ruminal fluid; and administering orally the sterilized ruminal fluid to a suckling calf.

BRIEF DESCRIPTION OF THE DRAWING

FIG. 1 shows a tabular comparison of initial body weight (IBW) and body weight gain (BWG) during each period of growth for experiments 2, 3 and 4.

FIG. 2 shows the effect of ruminal fluid (RF) preparations on the incidence and duration of scours in newborn calves.

FIG. 3 shows a tabular analysis of body weight gain (BWG) for experiments 2, 3, and 4 together.

FIG. 4 shows the composition of ruminal fluid preparations that were centrifuged to create cellular (RFC) and supernatant (RFS) fractions.

DETAILED DESCRIPTION OF THE INVENTION

The present invention utilizes a preparation of ruminal fluid to improve the health and growth of suckling dairy calves. This improvement in calf rearing allows for the extraction of a naturally occurring ruminal fluid from an adult cow. This fluid is readily available, and therefore, inexpensive. Our results indicate that ruminal fluid preparations improve the calves' average daily weight gain by as much as 100%, and the number of days that the calves had diarrhea was 5-fold lower. In addition, the ruminal fluid can be sterilized to negate the risks of pathogenic organisms populating the fluid. Because sterilized ruminal fluid preparations have as much activity as those containing live bacteria, disease transmission through administration of ruminal fluid should not be a problem. This research has thus elucidated a novel, safe mechanism for fighting disease, and provides an alternative to antibiotics.

The following experiments sought to examine the effect of ruminal fluid (RF) on the growth and health of new-born, milk-fed dairy calves. Ruminal fluid was fractionated by centrifugation and autoclaved so the mechanism of action could be more precisely defined.

Materials And Methods

Calves

A series of five (5) experiments were conducted over a period of 4-years (1998 to 2001) to examine the effects of RF extracts on calf health and growth. Research was implemented at the Cornell University Research Center in Dryden, N.Y. Pregnant, non-lactating Holstein dairy cattle were fed a total mixed ration (3.8 kg corn silage, 1.7 kg haylage, 2 kg grass hay, 1.2 kg high moisture shelled corn, 0.2 kg whole cottonseed, and 1.1 kg soybean meal/d) to meet NRC recommendations (NRC, 1989). Several hours before parturition, the pregnant cows were placed in a clean pen that was bedded with sawdust.

Soon after parturition (less than 15 minutes), the cow was milked, and 2 kg of colostrum was given to the new-born calf via a stomach tube. At approximately 1 hours after birth, the calf was given another 2 kg of colostrum orally. Calves were housed outside in individual hutches (approximately 1.7×1.2 m, Cal-Tel Delux, Hampel Corp., Germantown, Wis.). The hutches were located on clean, coarse gravel that was changed each year to prevent the build up of disease-causing microorganisms. Calves were given clean bedding (straw) each day, and manure was removed 3 times per week. Calves were raised under husbandry conditions that are typical of the Cornell Research Center, subject to the recommendations of the Cornell Center for Research Animal Resources (IACUC #91-32-00).

Calves were fed either milk or milk replacer and the amounts varied with the experiment. RF preparations and dosage time also varied with the experiments. Calves consumed all of the milk or milk replacer that was provided. All calves were provided with water and a commercial grain mix (Agway Calf Prestarter, Agway, Inc., Syracuse, N.Y., 22% crude protein, 81% TDN, 2.0 Mcal/1 kg, 1.3 Mcal/1 kg NEg) ad libitum starting at 3 days of age. Supplemental hay was not provided.

Body Weight Gain

Body weight gains were assessed according to the guidelines of Larson et al. (1977). Approximately 4 hours after birth, the calves were placed in a cart that restrained movement, the cart was placed on a platform scale, and initial body weight was determined as the difference between the weight of the cart and the total. Calves that had an initial birth weight greater than 53 kg or less than 34 kg were not included in the experiments. Thereafter, the calves were weighed in similar fashion approximately 6 hours after the morning feeding. The calves were restrained, and the weight measurements were relatively constant during the procedure (<0.25 kg variation).

Scours

The calves were inspected five times per day by the dairy farm workers (approximately 5 different individuals), and the appearance of feces on the hair surrounding the rectum and in the bedding was scored. In most cases, the calves defecated immediately after they were aroused. In other cases, fecal matter that had not yet dried or crusted over was used as an index of recent defecation. Scours were defined as fresh fecal material that had a runny or watery texture and either a white or gray color. According to Larsen et al. (1977), this definition corresponds to code 4 stools. If calves with scours appeared to be dehydrated (e.g., sunken eyes, sluggish body movements, and loss of skin elasticity), they were supplemented with an aqueous mixture of electrolytes (83% corn sugar, 4.3% sodium chloride, 4.8% potassium chloride, 4.9% sodium bicarbonate, 4% potassium phosphate, w/v).

Ruminal Fluid

Fresh ruminal fluid (FRF) for experiment 1 was removed from the rumen of a lactating dairy cow via a fistula. The fistulated cow was fed the total mixed ration (see above) ad libitum. The fluid was withdrawn from the rumen with a suction device via a pipe that had holes (as described in Example 1). The holes (6 mm diameter) in the pipe filtered the FRF so that it would not contain large feed particles. In experiments 2, 3 and 4, FRF was taken from a non-lactating dairy cow that was fed timothy hay ad libitum. The FRF was brought to the laboratory and placed in a 39° C. water bath. After gas production from the fermentation had buoyed feed particles to the top of the flask, and protozoa had sedimented to the bottom, FRF containing mixed ruminal bacteria was withdrawn from the center of the flask. The FRF was centrifuged (10,000×g, 30 min, 5° C.). The supernatant (RFS) was removed, and the cell pellet (RFC) was re-suspended in an equal volume of 0.9% NaCl. FRF that had been autoclaved (4 L, 121° C., 40 min) is referred to as autoclaved ruminal fluid (ARF). The ruminal fluid cell pellet (RFC), ruminal fluid supernatant (RFS) and ARF were dispensed into plastic vials (8 ml) and frozen (−15° C.) until use. Bacterial protein in RFC and RFS was analyzed by the method of Bradford (1967) (using bovine serum albumin as a standard) after the cells had been heated to 100° C. in 0.2 N NaOH for 15 min. The RNA and DNA were measured using an orcinol-FeCl3 reaction (Schneider, 1957) and ribose was used as the standard.

Bacterial Polysaccharide (BPS)

The FRF that had been centrifuged to remove feed particles (100×g, 5 min, 5° C.) was assayed by the phenol sulfuric acid method (0.3 ml phenol, 2.1 ml 70% (v/v) sulfuric acid, 100° C., 10 min, 485 nm; Ashwell, 1966) to estimate total FRF-BPS. The FRF was then centrifuged at higher speed to remove the bacteria (10,000×g, 15 min, 5° C.), and the resulting RFS was again assayed by the phenol sulfuric acid method to estimate RFS-BPS. The RFS was then treated with 1% (w/v) cetyltrimetylammonium bromide (CTAB) to precipitate bacterial polysaccharides (Ausubel et al, 1997), and the polysaccharide-free supernatant (PF-RFS) was also assayed by the phenol sulfuric acid method to estimate non-specific RF interference. Preliminary results indicated CTAB (200 μl of a 1% solution) did not interfere with the phenol sulfuric acid assay. True RFS-BPS was defined as RFS-BPS-PF-RFS. True RFC-BPS was defined as (FRF-BPS-PF-RFS)-true RFS-BPS. Glucose was used as a standard.

Experiment 1: Twenty four heifer calves were randomly allotted to control (no addition) or the FRF treatment (12 calves/group). Treated-calves received 8 ml FRF/day in the colostrum or morning milk feeding for 6 weeks. Both groups of calves were fed equal amounts of whole milk two times/day (approximately 12 hour interval between feedings, 4.5 kg/day). The calves were weaned at 6 weeks of age. Calves were weighed at birth and at 6 weeks of age.

Experiment 2: Thirty six heifer calves were randomly allotted to control (no addition), RFS or FRC treatments (12 calves/treatment). Treated-calves received 8 ml RFS or RFC/day in the colostrum or morning feeding for 42 days.

All 3 groups of calves were fed equal amounts of a commercially produced milk replacer (Excelerate, 30% protein, 20% fat, Milk Specialties Company, Dundee, Ill.) three times/day (approximately 8 hours interval between feedings, 7.5 kg/day). The calves were weaned at 6 weeks of age. Calves were weighed at birth and at 2, 4 and 6 weeks of age.

Experiment 3: A total of 24 heifer calves were randomly allotted to control (no addition) or the ARF treatment (12 calves/treatment). Treated calves received 8 ml ARF/day in the in the colostrum or morning milk feeding for 42 day. Both groups of calves were fed equal amounts of whole milk (6 kg/day, 2 feedings/day). The calves were weaned at 6 weeks of age. Calves were weighed at birth and at 2, 4 and 6 weeks of age.

Experiment 4: A total of 24 heifer calves was randomly allotted to control (no addition) or the ARF treatment (12 calves/treatment). Treated calves received 8 ml ARF/day in the colostrum or morning milk feeding for the first 5 days of life. Both groups of calves were fed equal amounts of milk replacer (7.5 kg/day, 3 feedings/day). The calves were weaned at 6 weeks of age. Calves were weighed at birth and at 2, 4 and 6 weeks of age.

Experiment 5: A total of 24 heifer calves was randomly allotted to control (no addition) or the ARF treatment (12 calves/treatment). Treated calves received 4 ml ARF immediately after birth. Both groups of calves were fed equal amounts of milk replacer (7.5 kg/day, 3 feedings/day). The calves were weaned at 6 weeks of age. Calves were weighed at birth and at 2, 4 and 6 weeks of age.

Statistics

The statistical analyses were performed by SAS (SAS Inst., Cary, N.C.). In the first analysis, the GLM procedure was used to analyze the weight gain in a completely randomized design (CRD) with analysis of covariance (ANCOVA), as described by Kuehl (2000) for each period of growth. Initial body weight was used as the covariate. The interaction between treatments and the covariate was used to check the uniformity of the slopes among treatments using the sequential sum of squares (Littell et al., 1991); the interaction and (or) the covariate were removed from the statistical model if not significant at P<0.05. The partial sum of squares was used in the ANCOVA to test treatments (Littell et al., 1991). The statistical model is shown below:

$$Y_{ij} = \mu + \tau_i + \beta(X_{ij} - \bar{X} \ldots) + e_j$$

Where Y is the body weight gain in each period, $\mu$ is the overall body weight gain mean, $\tau_i$ is the fixed effect of treatments, $\mu_1$ is the coefficient for the linear regression of Y on X, X is the initial body weight, and eij is the independent, identical, and normally distributed random experimental error.

In the second analysis, the weight gain of each growth period was analyzed as a Repeated Measure Design (RMD) for all experiments (except Experiment 1). The Mauchly sphericity test of the Proc GLM (SAS Inst., Cary, N.C.) was used to test the variance-covariance matrix and a univariate analysis of variance was performed if P>0.05. The treatment comparison was performed by contrast analysis. The Split-Plot statistical model used is described below (Kuehl, 2000).

$$Y_{ijk} = \mu + \alpha_i + d_{i,k} + \beta_j + (\alpha\beta)_{ij} + e_{ijk}$$

Where $\mu$ is the general mean, $\alpha_i$ is the fixed effect of treatment, $d_{i,k}$ is the random experimental error for calves within treatments to test treatment effect, $\beta_j$ is the effect of time (period of growth), $(\alpha\beta)_{ij}$ is the interaction between treatment and time, and $e_{ijk}$ is the normally distributed random experimental error.

In the third statistical analysis, all experiments were analyzed together, and treatments had two levels: control and treated, which consisted of calves that received any form of RF. Experiments were considered as blocks. Experiments 2, 3, 4 and 5 were used to investigate the effect of RF on weight gain of each week period. All experiments were used in the overall weight gain (0 to 6 weeks). In this overall analysis, milk intake was used as a covariate, and the analysis was similar to that described above. Because a preliminary study indicated an interaction between treatment and the covariate (milk intake), a model with unequal slopes was used (Littell et al., 1999). All analyses were performed by Proc MIXED (SAS Inst., Cary, N.C.), and the statistical model is shown below.

$$Y_{ij} = \alpha_i + \beta_i X_{ij} + b_j + e_{ij}$$

Where $\alpha_i$ is the intercept of the $i^{th}$ treatment effect, $\beta_i$ is the slope of the regression of weight gain on milk intake of the $i^{th}$ treatment, $b_j$ is the random effect of experiments, and $e_{ij}$ is the experimental random error.

The plot of studentized residues against the predicted values from the analysis of covariance was used to identify outliers, and the plot of the studentized residues against treatments was analyzed to test the assumption of identical variance (Kuehl, 2000). The normal distribution was also investigated (not shown).

Because a preliminary analysis of the number of day that calves had scours (scour days) was not normally distributed, a non-parametric test using the Proc NPAR1WAY of SAS (SAS Inst., Cary, N.C.) was selected to compare the distributions of each treatment (Snedecor and Cochran, 1971). Treatment comparisons were done by the Wilcoxon score and Kruskal-Wallis tests (SAS Inst., Cary, N.C.) without the continuity correction.

Results

Experiment 1: A preliminary experiment was conducted to ascertain the effect of FRF on the body weight gain and incidence of scours. Control calves that did not receive FRF had an initial body weight of 41.7+1.3 kg, and the total weight gain (0 to 6 weeks) was 16.5+1.0 kg. Treated calves (n=12) that were given the same amounts of milk and FRF for 42 day had an initial body weight of 43.4+4.9 kg, and the total weight gain (0 to 6 weeks) was 24.3+1.1 kg. The interaction between treatment (FRF) and the covariate (initial body weight) was not significant (P>0.05), the slope of the observed variable on initial weight (covariate) was similar, outliers were not identified, and treated-calves gained more weight than the controls (P<0.05). None of these control calves died, but most of them (10 out 12) had scours during the first two weeks (FIG. 2). The incidence of scours declined during the second and third periods of the trial (2 to 4 and 4 to 6 weeks), but the average number of day that each calf had scours was 2.67. Some FRF-treated calves scoured, but the average number of scour day was 3-fold less (P<0.05).

Experiment 2: Because results from experiment 1 indicated that FRF had a positive impact, we fractionated the RF and determined body weights at 2 week intervals. Control calves gained more weight in the second (2 to 4 weeks) and third growth periods (4 to 6 weeks) than the first period (0 to 2 weeks), and the total gain was 23.7 kg (FIG. 1). All of the control calves (12 out of 12) scoured during the first two-week period, but the incidence of scours declined as the calves became older (FIG. 2). Control calves had 2.75 scour days/calf.

Calves given RFS gained more weight than the untreated controls (P<0.05), and this overall advantage (0 to 6 weeks)

could be explained by an improvement in the first 2 weeks (P<0.05). During the second and third growth periods, RFS-treated calves did not gain more weight than the untreated calves (P>0.05). RFS-treated calves had fewer scours than untreated calves (FIG. 2, P<0.05).

Calves given RFC that had been resuspended in a similar volume of sodium chloride gained more weight in the first growth period (0 to 2 weeks) (P<0.05), but the overall gain (0 to 6 weeks) was not statistically improved relative to the control calves (P=0.06). The RFC-treated calves had fewer scours than untreated calves (FIG. 4, P<0.05).

Experiment 3: Because results from experiment 2 indicated even RFS could have a positive impact, we then examined the effect of ARF. Control calves had a total gain of 21.5 kg (FIG. 1), and the average number of scour day was 1.83 (FIG. 2). Calves given ARF gained more weight than untreated controls (0 to 6 weeks, P<0.05), and this advantage can be explained by an improvement in the first time period (P<0.05, FIG. 1). Calves that received ARF had fewer scours than untreated controls (FIG. 2, P<0.05).

Experiment 4: Because results from experiment 3 indicated even ARF could have a positive impact, we then decided to decrease the treatment period from 42 to 5 days. Control calves had a total gain of 22.0 kg (FIG. 1), and the average number of scour days was 3.67 (FIG. 2). Calves given ARF for only 5 days gained more weight (P<0.05) in the first growth period (0 to 2 weeks), but the overall gain (0 to 6 weeks) was not statistically improved (P=0.14). Calves that received ARF for 5 days had fewer scours than untreated controls (P<0.05).

Experiment 5: Because results from experiment 4 indicated that 8 ml of ARF for 5 days has a positive impact on calf health, we then decided to decrease the ARF to 4 ml and administered only one dose, immediately after birth. Control calves had a total gain of 22.2±4.05 kg, and the gains for the first (0 to 2 weeks) second (2 to 4 weeks) and third (4 to 6 weeks) periods were 2.84±1.85, 9.21±3.41 and 9.77±3.23 kg, respectively. Control calves had an average number of scour days of 1.81±1.99 days. Treated calves had a total gain of 25.3±4.25 kg, and the gains for the first (0 to 2 weeks), second (2 to 4 weeks) and third (4 to 6 weeks) periods were 5.34±2.66, 9.02±3.20 and 10.95±1.85 kg, respectively. Treated calves had an average number of scour days of 0.05±0.80 days. The overall increase in gain (0 to 6 weeks) and gains during the first period (0 to 2 weeks) were statistically significant (P<0.10 and P<0.05, respectively), but the gains during the second (2 to 4 weeks) and third (4 to 6 weeks) periods were not significantly different (P>0.05 or 0.10). The decrease in scour days was statistically significant (P<0.05).

Pooled Experiments: The analysis of pooled body weight gains from experiments 2, 3 and 4 are shown in FIG. 3. Similar to the individual analysis of each experiment, the analysis of pooled experiments indicated the administration of RF affected the first 2 weeks of growth (P<0.05), but RF had no effect on gain in subsequent time periods (P>0.05).

Discussion

The experiments described above were conducted over a 4 year period, and during this time the standard management procedures at the Cornell Research Center changed: 1) calves in the first and third studies were given whole milk, but experiments 2 and 4 were conducted with commercial milk replacers, 2) the intake of milk or milk replacer was varied from 4.5 to 7.5 kg/day, and 3) calves in experiments 1 and 3 were fed twice per day, but calves in experiment 2, 4 and 5 were fed 3 times per day. However, within each experiment, control and RF-treated calves always were given the same amount and type of milk.

It has long been recognized that calf growth experiments often have an inherently high degree of variation (Kertz et al., 1984), therefore, we used relatively large numbers of calves (n=12 per treatment). However, RF-dependent improvements in body weight gain were much greater for experiment 1 than experiments 2 through 4 (FIG. 2). The RF-dependent improvements in body weight gain for experiments 2 through 4 were 13, 20 and 12%, respectively (FIG. 2), but experiment 1 seemed to have a 49% increase in growth.

To examine if the control group of experiment 1 was abnormal, we compared it to another independent group of 12 calves. These other calves were fed the same amount of milk (4.5 g/day), were raised during the same period, had identical management and did not receive RF, however, they gained more weight than the original controls (19.7+1.5 versus 16.5+1.0 kg, respectively, P<0.05), even though the number of scour days was similar (2.51 versus 2.67, respectively, P>0.05). When this independent control was compared to the RF-treatment group the improvement was only 23%, a value that more closely resembled the effects seen in the other experiments.

Previous workers used fecal appearance as an index of calf scours and health, and we used a similar scoring system (Larson et al., 1977). Kertz et al. (1984) reported that 95% of their neonate calves had scours, the average number of scour d/calf for the control group was 4.5. In our studies (experiments 2 to 4), 86% of the control calves had scours, the average scour days were 2.8. We did not determine the cause of scours in our calves, but specific causes of diarrhea in calves are "difficult to establish" and are confounded by the fact that: 1) scours can be caused by many different viruses, bacteria and protozoa, 2) the mere presence of a potential pathogen in the feces does not always mean that it is the disease causing agent, 3) pathogens can operate in a synergistic and unpredictable fashion, and 4) scours are sometimes caused by digestive upsets rather than pathogens per se (Waltner-Toews et al., 1987; Steiner et al., 1997; Davis and Drackley, 1998).

All of our calves were given colostrum immediately after birth via a stomach tube, and this practice should have ensured passive immunity. When colostrum is fed immediately after birth, IgG concentrations in calf blood are proportional to the amount of colostrum fed (Morin et al., 1997). Some researchers have fortified colostrum by vaccinating cows with viral and bacterial antigens prior to calving (Acres et al., 1979; Snodgrass et al., 1982; Saif et al., 1983), and calves given the same pathogens have sometimes had better weight gains and less diarrhea. However, in practice, fortified colostrum is often without effect (Tizard, 1996).

Based on the previous literature (Pounden and Hibbs, 1949 a,b)., we had originally hypothesized that FRF might act as a probiotic, and FRF decreased the incidence and duration of scours (P<0.05) and increased body weight gain (P<0.05). However, subsequent experiments indicated that cells harvested by centrifugation, re-suspended in sodium chloride and frozen aerobically without a cryo-protectant could promote growth (P<0.05) and decrease scours (P<0.05). The idea that FRF was a probiotic was further contradicted by the observation that RFS or even ARF increased body weight gain (P<0.05) and decreased scours (P<0.05).

Ruminal fluid contains microbial proteins, volatile fatty acids and vitamins, but it is very unlikely that our response was nutritional (FIG. 4). The amount of bacterial protein was very small (approximately 8 mg/d), and even RFS that had been centrifuged to remove virtually all of the bacteria had activity (P<0.05). Because RFC also had activity (P<0.05), the benefit could not be explained by volatile fatty acids from the fluid phase.

When FRF was harvested by centrifugation, there was a distinct layer of polysaccharide (slime) directly above the cell pellet, and RFS was clear. Subsequent work, however, indicated that even RFS had an abundance of BPS that could be precipitated by CTAB (FIG. 4), an anionic detergent that has been used to precipitate BPS and "cleanup" DNA preparations (Ausubel et al., 1997). Because BPS's are potent antigens and retain activity after autoclaving (Tizard, 1996), it appears that BPS is the active ingredient in RF.

In the 1990's, Nosky and Worthington developed a product based on mycobacterium cell walls under the trade name Immunoboost (Veterphram Research Inc, Athens, Ga. and Chino Corona Veterinary Services, Chino, Calif.). Their work indicated that calves given intravenous, intramuscular and subcutaneous injections of Immunoboost during the first 24 hours of life had fewer scours and higher ADG than untreated controls. Oral administration was not tested, but the authors noted that Immunoboost-treated calves required 17% less antibiotic treatment.

Previous attempts to improve calf health have tried to enhance passive immunity (Acres et al., 1979; Snodgrass et al., 1982; Saif et al, 1983), but it should be noted that calves usually die from dehydration rather than microbial infection per se (Tizard, 1996; Davis and Drackley, 1998). Newborns are very prone to diarrhea, and this condition is triggered by agents that irritate the intestine (Guyton, 1971). Intestinal irritation increases secretion, motility, and stool volume. As the animal becomes older and the intestine is repeatedly exposed to irritants and antigens, the intestinal tissues become desensitized, and the frequency of diarrhea declines (Ernst et al., 1988).

Intestinal de-sensitization (sometimes called oral tolerance) is a localized phenomenon that is mediated by circulating immunoglobulins and the macrophages (Fahmi and Chaby, 1993, 1994). When macrophages are presented with antigens bound to immunoglobulins, they secrete cytokines that can directly affect mammalian cells (Kaufman et al., 2000). Cytokines appear to accelerate intestinal maturation and de-sensitization, and this process is dose-dependent. Studies with food allergens have shown that low doses invoke limited suppression, but large doses can provoke clonal anergy and immunotolerance (Roitt, 1998, Tizard, 1996).

Because RF has a highly diverse population of bacteria and other microorganisms (Krause and Russell, 1996), it would contain dozens, perhaps hundreds, of different BPS molecules. The activity of RF does not seem to be highly diet-dependent. The FRF (experiment 1) was obtained from a cow fed a typical dairy cattle ration, but the cow that served as a donor for experiments 2, 3 and 4 was fed only timothy hay.

We originally gave the calves RF preparations each day until weaning (6 weeks), but the improvement in body weight gain and decrease in scours was greatest during the first 2 weeks of life (P<0.05, FIG. 2). Because the improvement in gain merely carried over into subsequent time periods (FIGS. 2 and 3), we decided to decrease the dosage time from 42 to 5 days (experiment 4). Calves given ARF for 5 days or even once on the first day of life also responded, and this result is consistent with the idea that RF is most beneficial to newborn calves that do not have a fully developed immune system.

Conclusions

Newborn dairy calves that are given daily doses of RF gain more weight and have fewer scours than untreated controls. Because even autoclaved preparations give a positive response, RF preparations do not act as a probiotic.

The observation that autoclaved RF preparations decrease scours as well as increase body weight gain has practical relevance: 1) RF preparations can be given orally via the milk, 2) RF contains naturally occurring non-pathogenic bacteria, 3) RF can be autoclaved to eliminate the chance of disease transmission, and 4) the time needed to demonstrate a response is relatively short (as little as 5 days).

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

References

Acres, S. D., R. E. Isaacson, and K. Babiuk. 1979. Immunization of calves against enterotoxigenic colibacillosis by vaccinating dams with purified K99 antigen and whole cell bacterins. Infect. Immun. 25:121–126.

Ashwell, G. 1966. The phenol sulfuric acid reaction for carbohydrates. Method in Enzymol. 8: 93–95.

Ausubel, F., R. Brent, R. E. Kinston, D. D. Moore, J. G. Seidman, J. A. Smith and K. Struhl, ed. 1997. Short Protocols in Molecular Biology. 3rd ed., page 2–13. John Wiley & Sons, Inc., New York.

Bradford, M. 1976. Photometric methods for protein determination. Procedures and Materials. Anal. Biochem. 72: 248–254.

Costerton, J. W., H. N. Damgaard, and J. -K. Cheng. 1974. Cell envelope morphology of rumen bacteria. J. Bacteriol. 118:1132–1143.

Davis, C. L. and J. K. Drackley. 1998. The Development, Nutrition and Management of the Young Calf. Iowa State University Press, Ames, Iowa.

Ernst, P. B., R. Scicchitano, B. J. Underdown, and J. Bienenstock. 1988. Oral Immunization and tolerance. Pages 125–144 in Immunology of the Gastrointestinal Tract and Liver. M. F. Heyworth and A. L. Jones, eds. Raven Press, New York. N.Y.

Fahmi, H., and R. Chaby. 1993. Desensitization of macrophages to endotoxin effects is not correlated with a down-regulation of lipopolysaccharide-binding sites. Cell. Immunol. 150:219–229.

Fahmi, H., and R. Chaby. 1994. Differential recovery of macrophages from endotoxintolerant states elicited by lipopolysaccharide and enzymatic treatments. Immunol. Investig. 23:243–258.

Guyton, A. C. 1971. Textbook of Medical Physiology. Pages 779–780. W. B. Saunders Co., Philadelphia, Pa.

Hungate, R. E. 1966. Pages 120–121 in The Rumen and Its Microbes. Academic Press, New York, N.Y.

Kaufman, A., D. Gemsa, and H. Sprenger. 2000. Differential desensitization of lipopolysaccharide-inducible chemokine gene expression in monocytes and macrophages. Eur. J. Immunol. 30:1562–1567.

Kertz, A. F., L. F. Reutzel, and J. H. Mahoney. 1984. Ad libitum water intake by neonatal calves and its relationship to calf starter intake, weight gain, feces score, and season. J. Dairy Sci. 67:2964–2969.

Krause, D. O., and J. B. Russell. 1996. How many ruminal bacteria are there? J. Dairy Sci. 79:1467–1475.

Kuehl, R. 0. 2000. Design of Experiments: Statistical Principles of Research Design and Analysis (2nd. Ed.). Duxbury Press, New York.

Larson, L. L., F. G. Owen, J. L. Albright, R. D. Applemeann, R. C. Lamb, and M. L.D. 1977. Guidelines toward more uniformity in measuring and reporting calf experimental data. J. Diary Sci. 60: 989–991.

Littell, R. C., R. J. Freund, and P. C. Spector. 1991. SAS System for Linear Models (3rd Ed.). SAS Institute Inc., Cary, N.C.

Littell, R. C., G. A. Milliken, W. W. Stroup, and R. D. Wolfinger. 1999. SAS System for Mixed Models. SAS Institute, Cary, N.C.

Morin, D. E, G. C. McCoy, and W. L. Hurley. 1997. Effects of quality, quantity, and timing of colostrum feeding and additional of dried colostrum supplement on immunoglobulin G1 absorption in dairy calves. J. Dairy Sci. 80: 747–753.

National Animal Health Monitoring System. 1993. Dairy herd management practices focusing on pre-weaned heifers. Ft. Collins Colo.: USDA:APHIS:VS.

National, Animal, Health, Monitoring and System. 1996. Part II changes in the U.S. dairy industry 1991 to 1996 Ft. Collins Colo.: USDA:APHIS:VS.

Nosky, B. J., and T. J. Worthington. (no date given). Effects of prophylactic administration of a nonspecific immune stimulant on the performance of hutch-reared calves. Veterphram Research Inc, Athens Ga. and Chino Corona Veterinary Services, Chino, Calif.

NRC. 1989. Nutrient Requirements of Dairy Cattle. National Academy Press, Washington, D.C.

Otterby, D. E. and J. G. Linn. 1981. Advances in nutrition and management of calves and heifers. J. Diary Sci. 64: 1365–1377.

Pounden, W. D., and J. W. Hibbs. 1949a. Rumen inoculations in young calves. J. Amer. Vet. Med. Assn. 114: 33–35.

Pounden, W. D., and J. W. Hibbs. 1949b. The influence of pasture and rumen inoculation on the establishment of certain microorganisms in the rumen of young dairy calves. J. Dairy Sci. 32:1025–1031.

Roitt, I., BrostoffJ, Male D, Immunology 5th ed. London: Mosby 1998.

Saif, L. J., D. R. Redman, and K. L. Smith. 1983. Passive immunity to bovine rotavirus in newborn calves fed colostrum supplements from immunized or non-immunized cows. Infect. Immun. 41:1118–1131.

Schneider, W. C. 1957. Determination of nucleic acids in tissues by pentose analysis. In S. C. a. N. 0. Kaplan (ed.), Methods in Enzymology., vol. III. Academic Press, New York.

Snedecor, G. W. and W. G. Cochran. 1971. Statistical Methods (6th Ed.). Iowa State University Press, Ames.

Snodgrass, D. R. 1982. Diarrhea in dairy calves reduced by feeding colostrum from cows vaccinated with rotavirus. Res. Vet. Sci. 32:70–73.

Steiner, L., A. Busarto, A. Burnens and C. Gaillard. 1997. Frequency and etiology of calf losses and diseases before weaning in cow-calf farms. II. Microbiological and parasitological diagnoses in diarrhoeic calves. DTW Deutsche-Tieraerztliche-Wochemschrift 104: 169–173.

Tizard, I. R. 1996. Pages 237–264. In Veterinary Immunology an Introduction. W. B. Saunders Co., Philadelphia, Pa.

Waltner-Toews, D., S. W. Martin and A. H. Meek. 1987. An epidemiological study of selected calf pahogens on Holstein dairy farms in southwesten Ontario. Can. J. Vet. Res. 50:307–313.

What is claimed is:

1. A method of improving the health of an immature animal, comprising the steps of:
    a) withdrawing gastrointestinal fluid from a mature animal;
    b) sterilizing said gastrointestinal fluid; and
    c) administering orally to an immature animal a composition selected from the group consisting of:
        i. said sterilized gastrointestinal fluid;
        ii. a composition derived from said sterilized gastrointestinal fluid;
        iii. a non-viable organism derived from said sterilized gastrointestinal fluid; and
        iv. a composition comprising a protein or polysaccharide derived from said organism.

2. The method of claim 1, wherein said oral administration step is performed within about 8 hours after birth of said immature animal.

3. The method of claim 2, wherein the average daily weight gain of said immature animal is increased, or the incidence of scours in said immature animal is decreased, or both.

4. The method of claim 1, wherein said sterilized gastrointestinal fluid is administered at least one time, in an effective amount consisting essentially of about 4 milliliters.

5. The method of claim 4, wherein the average daily weight gain of said immature animal is increased, or the incidence of scours in said immature animal is decreased, or both.

6. The method of claim 4, wherein said oral administration step is performed within about 8 hours after birth of said immature animal.

7. The method of claim 4, wherein said gastrointestinal fluid is sterilized by autoclaving.

8. A method of improving the health of a suckling calf, comprising the steps of:
    a) withdrawing ruminal fluid from a mature cow;
    b) sterilizing said ruminal fluid; and
    c) administering orally to said calf a composition selected from the group consisting of:
        i. said sterilized ruminal fluid;
        ii. a composition derived from said sterilized ruminal fluid;
        iii. a non-viable organism derived from said sterilized ruminal fluid; and
        iv. a composition comprising a protein or polysaccharide derived from said organism.

9. The method of claim 8, wherein said oral administration step is performed within about 8 hours after birth of said calf.

10. The method of claim 9, wherein the average daily weight gain of said calf is increased, or the incidence of scours in said calf is decreased, or both.

11. The method of claim 8, wherein said sterilized ruminal fluid is administered at least one time, in an effective amount consisting essentially of about 4 milliliters.

12. The method of claim 11 wherein the average daily weight gain of said calf is increased, or the incidence of scours in said calf is decreased, or both.

13. The method of claim 11, wherein said oral administration step is performed within about 8 hours after birth of said calf.

14. The method of claim 11, wherein said ruminal fluid is sterilized by autoclaving.

15. The method of claim 11, wherein said ruminal fluid is clarified prior to sterilizing.

16. The method of claim 11, wherein said sterilized ruminal fluid is frozen.

17. The method of claim 8, wherein paid sterilized ruminal fluid, composition or non-viable organism is dried prior to administration.

18. The method of claim 11, wherein said ruminal fluid is mixed with a preservation fluid prior to sterilizing.

19. The method of claim 18, wherein said preservation fluid comprises a glycerol salt solution.

20. The method of claim 18, wherein the average daily weight gain of said immature animal is increased, or the incidence of scours in said immature animal is decreased, or both.

* * * * *